US006516277B2

(12) United States Patent
Edgecombe et al.

(10) Patent No.: US 6,516,277 B2
(45) Date of Patent: *Feb. 4, 2003

(54) METHOD FOR DETERMINING MULTI-DIMENSIONAL TOPOLOGY

(75) Inventors: Kenneth E. Edgecombe, Kingston (CA); Alan D. Ableson, Kingston (CA)

(73) Assignee: Queen's University at Kingston, Kingston (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/061,257

(22) Filed: Feb. 4, 2002

(65) Prior Publication Data

US 2002/0111761 A1 Aug. 15, 2002

Related U.S. Application Data

(63) Continuation of application No. 09/086,593, filed on May 29, 1998, now Pat. No. 6,345,235.
(60) Provisional application No. 60/048,067, filed on May 30, 1997, and provisional application No. 60/059,563, filed on Sep. 19, 1997.

(51) Int. Cl.$^7$ .............................................. G06F 19/00
(52) U.S. Cl. ............................. 702/27; 702/21; 702/28; 702/32; 702/179; 702/180
(58) Field of Search .............................. 702/27, 21, 28, 702/32, 179, 180; 703/1, 7, 11, 12, 2

(56) References Cited

U.S. PATENT DOCUMENTS

| | | | | |
|---|---|---|---|---|
| 5,424,963 A | * | 6/1995 | Turner et al. ................ 364/578 |
| 5,510,838 A | * | 4/1996 | Yomdin et al. ........... 348/384.1 |
| 5,596,135 A | * | 1/1997 | Mito et al. ................. 73/23.35 |
| 5,600,571 A | * | 2/1997 | Friesner et al. ............. 364/496 |
| 5,764,872 A | * | 6/1998 | Koyamada et al. ......... 395/140 |
| 5,884,230 A | * | 3/1999 | Srinivasan et al. ........... 702/22 |
| 5,930,784 A | * | 7/1999 | Hendrickson .................. 707/2 |
| 6,014,449 A | * | 1/2000 | Jacobs et al. .................. 382/0 |
| 6,035,057 A | * | 3/2000 | Hoffman ..................... 382/159 |
| 6,037,949 A | * | 3/2000 | DeRose et al. ............. 345/430 |
| 6,064,945 A | * | 5/2000 | Gorenstein et al. ........... 702/23 |
| 6,128,582 A | * | 10/2000 | Wilson et al. ................. 702/27 |
| 6,131,072 A | * | 10/2000 | Holden et al. ................ 702/20 |

OTHER PUBLICATIONS

Aray, Y., et al., "Numerical Determination of the Topological Properties of the Electronic Charge Density in Molecules and Solids Using Density Functional Theory", *J. Phys. Chem.* 101: 6976–6982 (1997).

(List continued on next page.)

*Primary Examiner*—Marc S. Hoff
*Assistant Examiner*—Carol S. W. Tsai
(74) *Attorney, Agent, or Firm*—Robert H. Wilkes; Carol Miernicki Steeg; Dowell & Dowell, P.C.

(57) ABSTRACT

This invention relates to methods and apparatus for determining the multi-dimensional topology of a substance (system) within a volume (space). A method according to a preferred embodiment of the invention comprises the steps of: acquiring a set of relative values for the density (scalar properties) of the volume, each value for a given location (point) within the volume; interpolating a set of functions to generate a continuous relative density for the volume; identifying critical points of the continuous relative density by using an eigenvector following method; and associating critical points with one another by following a gradient path of the continuous relative density between the critical points. The method is applicable to a wide range of data relating to fields such as crystallography, fluid dynamics, edge detection, and financial markets, to determine the topology of structures contained therein.

10 Claims, 2 Drawing Sheets

OTHER PUBLICATIONS

Bader, R.F.W., et al., "Molecular Structure and Its Change: Hydrocarbons", *J. Am. Chem. Soc.,* 104: 940–945 (1982).

Bader, R. F. W., et al., "Quantum Topology of Molecular Charge Distributions. II. Molecular Structure and Its Change", *J. Chem. Phys.* 70(9): 4316–4329 (1979).

Bader, R. F.W., "Atoms in Molecules A Quantum Theory", Clarendon Press—Oxford, pp. 1–52 (1990).

Baker, J., "An Algorithm for the Location of Transition States", *J. Comput. Chem.* 7: 385–395 (1986).

Banerjee, A., et al., "Search for Stationary Points on Surfaces", *J. Phys. Chem. 89:* 52–57 (1985).

Bartels, R. H. et al., "Rendering and Evaluation". In An Introduction to Splines for use in Computer Graphics and Geometric Modeling, Morgan Kaufmann Publishers, Los Altos, Chapter 20, (1987).

Cerjan, C.J., et al., "On Finding Transition States", *J. Chem. Phys.* 75: 2800–2803 (1981).

Chorafas, D. N., "The Development and Use of Proprietary Models for Pricing the Trading Book" In *The Market Risk Amendment.* McGraw–Hill, Toronto, Chapter 16, pp. 285–305 (1998).

Destro, R., et al., "Total Electronic Charge Denisty of L–alanine from X–ray Diffraction at 23 K", *Chem. Phys. Letters* 186: 47–52 (1991).

Gatti, C., et al., "Crystal Field Effects on the Topological Properties of the Electron Density in Molecular Crystals: The Case of Urea", *J. Chem. Phys. 101:* 10686–10696 (1994).

Leherte, L. et al., "Molecular Scene Analysis: Application of a Topological Approach to the Automated Interpretation of Protein Electron–Density Maps", *Acta Cryst.* D50: 155–166 (1994).

Leherte, L., et al., "Analysis of Three–Dimensional Protein Images", *J. Artif. Intell. Res.* 7: 125–159 (1997).

Mei, C., et al., "Topological Analysis of the Charge Density of Solids: bcc Sodium and Lithium", *Int. J. Quantum Chem.,* 48: 287–293 (1993).

Pollard, A., et al., "Flow Topology of Turbulent Flow over a Forward Facing Step", Proceedings of the $4^{th}$ Annual Conference of the CFD Society of Canada, pp. 263–270 (1996).

Popelier, P.L.A., "A Robust Algorithm to Locate Automatically all Types of Critical Points in the Charge Density and its Laplacian", *Chem. Phys. Lett.* 228: 160–164 (1994).

Popelier, P.L.A., "MORPHY, a Program for an Automated "Atoms in Molecules" Analysis", *Comput. Phys. Comm. 93:* 212–240 (1996).

Simons, J., et al., "Walking on Potential Energy Surfaces", *J. Phys. Chem., 87:* 2745–2753 (1983).

Sousa, C., et al., "Topological Analysis of Charge Density in Ionic Solids", *Chem. Phys. Letters,* 215: 97–102 (1993).

\* cited by examiner

METHOD FOR DETERMINING MULTI-DIMENSIONAL TOPOLOGY

RELATED APPLICATIONS

This application is a continuation of allowed U.S. patent application Ser. No. 09/086,593 filed May 29, 1998, now U.S. Pat. No. 6,345,235, which claims the benefit of priority of U.S. Provisional Patent Applications No. 60/048,067, filed May 30, 1997, and No. 60/059,563, filed Sep. 19, 1997. The contents of each of these applications is hereby incorporated by reference.

FIELD OF THE INVENTION

This invention relates to methods for determining the multi-dimensional topology of a system, and in particular, to methods for identifying critical points in the internal multi-dimensional topology of a system within a space.

BACKGROUND OF THE INVENTION

Complex data sets such as scalar fields or relative density maps exist in virtually every area of science. Fluid dynamics, stress analysis, quantum physics, physical chemistry, molecular biology, and geology are but a few examples. These data contain information relating to the multi-dimensional topology of a structure, such as a molecule, the spacial arrangement of ore veins within a geological sample, etc., as the case may be. However, the accuracy of the information extracted is limited by the strength of the analysis applied to the data.

As an example, consider the 3-dimensional topology of the molecular structure of proteins. Although elucidation of the molecular structure of proteins is a fundamental goal of research in molecular biology, only a small fraction of the currently known proteins have been fully characterized. Crystallography plays a major role in current efforts to characterize and understand molecular structures and molecular recognition processes. Typically, a pure crystal of a protein residing in a volume under consideration is irradiated with X-rays to produce a diffraction pattern on a photographic film located on the opposite side of the crystal. Following a series of chemical and mathematical manipulations, a series of electron density maps are created, and these may be blended or combined to form an electron density map of a single protein molecule. The information derived from crystallographic studies provides a molecular scene, the starting point for analyses.

The determination of molecular structures from X-ray diffraction data is an exercise in image reconstruction from incomplete and/or noisy data. Molecular scene analysis is therefore concerned with the processes of reconstruction, classification and understanding of complex images. Such analyses rely on the ability to segment a representation of a molecule into its meaningful parts, and on the availability of a priori information, in the form of rules or structural templates, for interpreting the partitioned image.

A crystal consists of a regular (periodic) 3D arrangement of identical building blocks, termed the unit cell. A crystal structure is defined by the disposition of atoms and molecules within this fundamental repeating unit. A given structure can be solved by interpreting an electron density image of its unit cell content, generated—using a Fourier transform—from the amplitudes and phases of experimentally derived diffraction data.

An electron density map is a 3D array of real values that estimate the electron density at given locations in the unit cell; this information gives access to the structure of a protein. Strictly speaking, the diffraction experiment provides information on the ensemble average over all of the unit cells. Unfortunately, only the diffraction amplitudes can be measured directly from a crystallographic experiment; the necessary phase information for constructing the electron density image must be obtained by other means. Current solutions to the phase problem for macromolecules rely on gathering extensive experimental data and on considerable input from experts during the image interpretation process. This is the classic phase problem of crystallography.

In contrast to small molecules (up to 150 or so independent, non-hydrogen atoms), the determination of protein structures (which often contain in excess of 3000 atoms) remains a complex task hindered by the phase problem. The initial electron density images obtained from crystallographic data for these macromolecules are typically incomplete and noisy. The interpretation of a protein image generally involves mental pattern recognition procedures where the image is segmented into features, which are then compared with anticipated structural motifs. Once a feature is identified, this partial structure information can be used to improve the phase estimates resulting in a refined (and eventually higher-resolution) image of the molecule. Despite recent advances in tools for molecular graphics and modeling, this iterative approach to image reconstruction is still a time consuming process requiring substantial expert intervention. In particular, it depends on an individual's recall of existing structural patterns and on the individual's ability to recognize the presence of these motifs in a noisy and complex 3D image representation.

OBJECT OF THE INVENTION

It is an object of the present invention to provide methods for determining the multi-dimensional topology of a system, such as a system within a space.

SUMMARY OF THE INVENTION

According to a broad aspect of the invention there is provided a method of determining the multi-dimensional topology of a substance within a volume, the method comprising the steps of:
 a) acquiring a set of relative density values for the volume, each value for a given location within the volume;
 b) interpolating a set of functions to generate a continuous relative density for the volume;
 c) identifying critical points of the continuous relative density by using an eigenvector following method; and
 d) associating critical points with one another by following a gradient path of the continuous relative density between the critical points.

According to another aspect of the invention, there is provided a method of determining the multi-dimensional topology of a volume from a set of relative density values for the volume, each value for a given location within the volume, the method comprising the steps of:
 a) interpolating a set of functions to generate a continuous relative density for the volume;
 b) identifying critical points of the continuous relative density by using an eigenvector following method; and
 c) associating critical points with one another by following a gradient path of the continuous relative density between the critical points.

The invention further provides a method of determining the multi-dimensional topology of a volume, having a continuous relative density for the volume generated from a set of functions interpolating a set of acquired relative density values for the volume, each value for a given location within the volume, the method comprising the steps of:

a) identifying critical points of the continuous relative density by using an eigenvector following method; and b) associating critical points with one another by following a gradient path of the continuous relative density between the critical points.

The invention further provides a method of identifying critical points in the multi-dimensional topology of a substance within a volume, the method comprising the steps of:

a) acquiring a set of relative density values for the volume, each value for a given location within the volume;

b) interpolating a set of functions to generate a continuous relative density for the volume; and c) identifying critical points of the continuous relative density by using an eigenvector following method.

According to a further aspect of the invention, a method is provide for determining the multi-dimensional topology of a system within a space, the method comprising the steps of:

a) acquiring a set of relative values for scalar properties of the space, each value for a given point within the space;

b) interpolating a set of functions to generate continuous relative values for the scalar properties;

c) identifying critical points of the continuous relative values by using an eigenvector following method; and d) associating critical points with one another by following a gradient path of the continuous relative values between the critical points.

The invention also provides a method of determining the multi-dimensional topology of a system within a space from a set of relative values for scalar properties of the space, each value for a given point within the space, the method comprising the steps of:

a) interpolating a set of functions to generate continuous relative values for the scalar properties;

b) identifying critical points of the continuous relative values by using an eigenvector following method; and c) associating critical points with one another by following a gradient path of the continuous relative values between the critical points.

The invention further provides a method of determining the multi-dimensional topology of a system within a space, having continuous relative values of scalar properties for the space generated from a set of functions interpolating a set of acquired relative values of the scalar properties, each value for a given location within the space, the method comprising the steps of:

a) identifying critical points of the continuous relative values by using an eigenvector following method; and b) associating critical points with one another by following a gradient path of the continuous relative values between the critical points.

The invention further provides a method of identifying critical points in the multi-dimensional topology of a system within a space, the method comprising the steps of:

a) acquiring a set of relative values for properties of the space, each value for a given point within the space;

b) interpolating a set of functions to generate continuous relative values for the space; and c) identifying critical points of the continuous relative values by using an eigenvector following method.

The methods of the invention also provide the ability to generate a representation of the topology according to the associated critical points.

According to the invention, in any of the above methods:

a) the substance may be a protein or a protein complex; and b) the relative density values may be electron density values generated by x-ray diffraction through a crystal of the protein or protein complex.

According to the invention, the relative density can be the electron charge density resulting from the application of X-ray crystallography to proteins. The methods of the invention can also be applied to other systems that can be represented in terms of relative values of properties. For example, relative values of properties may be relative density or concentration of ore derived from core samples of mineral deposits in geological analysis. The samples provide the values of relative density or concentration at given points (in this case, locations) within the space (in this case, a volume) to be analyzed. The result of the application of the method of the invention in this case may be to find regions of low concentration (minima), high concentration (maxima), and other critical points of an ore body within the space; in order to define the ore body and/or its path.

As other examples, the systems may be the flow of a fluid over a surface, the reaction and/or folding of a protein or protein complex, an edge portion of a graphical image, one or more extremal points within a scalar field, or a trend or energy field within a set of data.

In further aspects, the invention provides separate means for carrying out each of the method aspects.

BRIEF DESCRIPTION OF THE DRAWINGS

For a better understanding of the present invention, and to show more clearly how it may be carried into effect, reference will now be made, by way of example, to the accompanying drawings, which show example systems and critical points for the present invention, and in which:

FIG. 1($b$) is an electron density map viewed at 3 Ang;

FIG. 1($c$) is an electron density map viewed at 5 Ang; and

DETAILED DESCRIPTION OF THE PREFERRED EMBODIMENT

Figure 1:
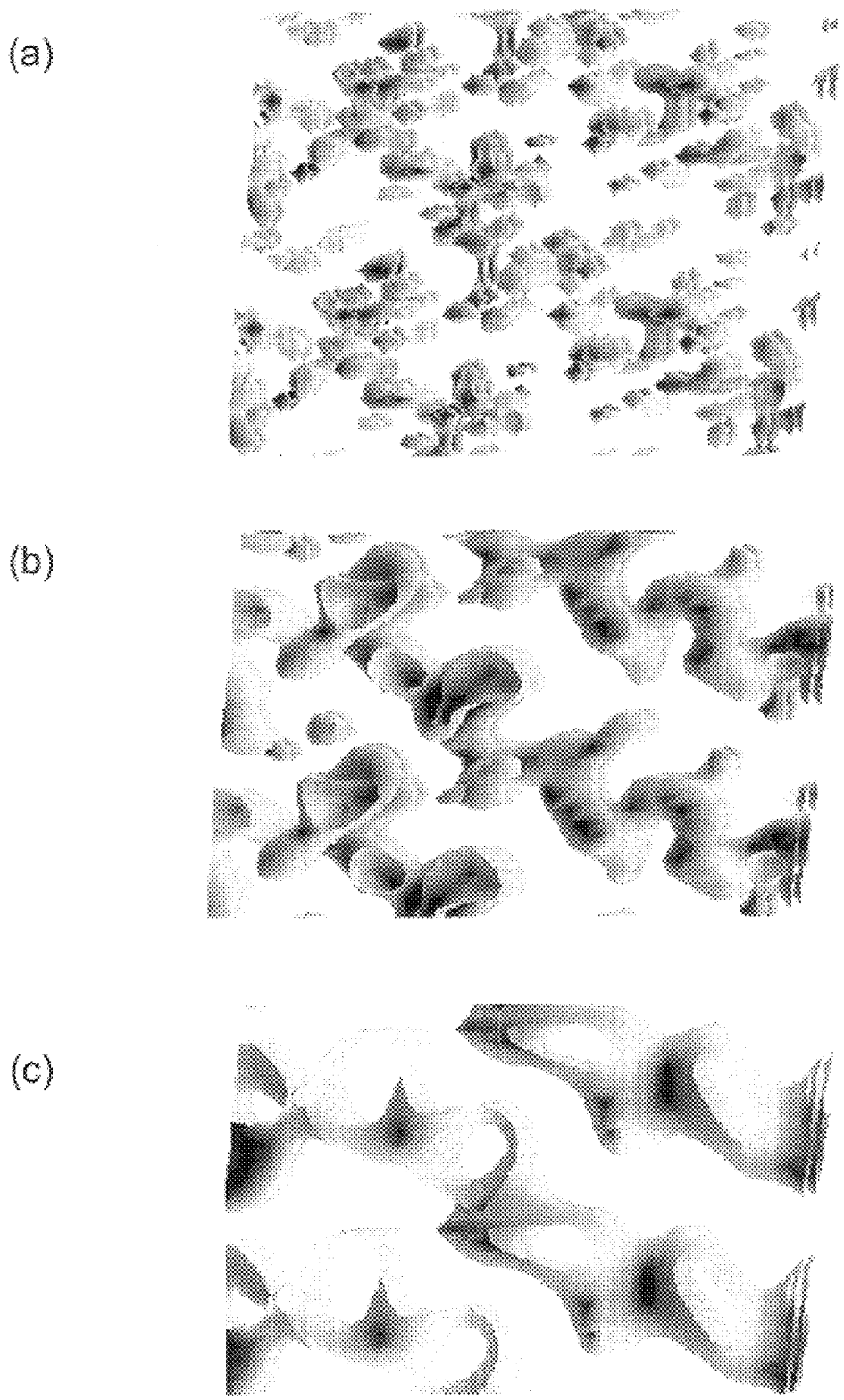
FIG. 1($a$) is an electron density map viewed at 1 Ang.

The preferred embodiment relates generally to methods for determining the multi-dimensional topology of a system within a space. As used herein, the term space means any multi-dimensional space that may be represented by a set of relative values for scalar properties of the space. For example, a space can be physical, i.e., comprised of matter, in which case the relative values can be generated by any suitable means, and relative values respecting density and concentration are but two examples. A space can also be non-physical, in which case relative values describing the space do not correspond to any physical matter. Accordingly, the invention is equally applicable to the analysis of any type of space, and provides for the determination of a system contained therein.

As used herein, the term system means any structure or trend within a space. A system within a space is represented by at least a portion of the set of relative values for scalar properties of the space within which it is located. Accordingly, by one aspect the invention relates to the determination of the relative values which represent a system within a space. By a further aspect, the invention relates to the determination of the multi-dimensional topology of a system within a space. The determination of the topology of the system is based on the determination of the corresponding relative values.

The present invention is applicable to diverse fields such as, but not limited to, fluid dynamics, strews analysis, quantum physics, physical chemistry, molecular biology, and geology, in which underlying multi-dimensional static or dynamic systems physically exist. The invention is also applicable to any discipline where detection of non-physical multi-dimensional systems within complex data sets is required, such as economics and demographics.

Examples of systems are, in the case of molecular biology, a crystal, such as that formed from a pure protein, and in the case of geology, a vein such as an ore vein. Specifically, in these examples, system refers to the multi-dimensional topology of the molecular structure of a protein, and the multi-dimensional path of an ore vein through its surrounding space (rock, et.). Relative values for scalar properties of these systems and the space in which they exist can be obtained via any suitable means, as are well known in the art in the case of a protein crystal, the relative values can be relative density values obtained from, for example, the electron charge density obtained from X-ray crystallography techniques. In the case of an ore vein, the relative values can be relative concentration of the ore, obtained from a series of core samples.

Applying the methods of the preferred embodiment to the determination of protein structure, for example, yields a substantial advantage over conventional methods. In a series of electron density maps corresponding to a protein under consideration and generated via crystallography techniques, lines become closer together as electron density increases. In a conventional analysis, these maps are analyzed to determine whether the "peaks" and "valleys" visualized correspond to the backbone of the protein, or to the side chains that protrude from the protein backbone. This iterative approach to image reconstruction is a time-consuming process requiring substantial expert intervention, and it relies on an individual's recall of existing structural patterns and on the individual's ability to recognize the presence of these motifs in a noisy and complex 3D image representation.

In contrast, the preferred embodiment provides a determination of which points are connected along the backbone of the protein, and which points are protruding from the backbone as side chains. According to a preferred embodiment of the invention, a set of relative density values are acquired for different points through a sample volume. A set of functions is used to interpolate continuous relative density values for the volume from the acquired relative density values. An eigenvector-following method is employed to locate all critical points in a unit cell (volume) of the sample. A gradient path ascent method is then employed to examine each pass and determine its associated peaks along the backbone (i.e., the connectivity among the critical points). In general, a pass has at least two associated peaks, and in the majority of cases, there are two associated peaks.

As used herein, for 3-dimensional cases, the term "critical points" means minima, maxima, and saddle points, wherein there are two types of saddle points: passes and pales. These critical points are points where the magnitude of the first derivative of a value, such as a relative density value, is equal to zero.

In applying the methods of the preferred embodiment to the analysis of three-dimensional protein images, reference is made to Example 1. For instance, a description of electron density (relative density) acquisition through X-ray crystallography, and an introduction to interpolation of functions to generate continuous electron density are contained in Example 1. A description of charge density and its relationship with protein structure, including a discussion of critical points, is contained in Bader, R. F. W. (1990) *Atoms in Molecules: A Quantum Theory*, Clarendon Press, Oxford, pp. 16–20.

The contents of all publications cited in this description are incorporated herein by reference in their entirety.

Preferred embodiments of the interpolating step as applied to the domain of protein structure determination which describes the generation of continuous electron density using polynomial splines are contained in Example 2.

Preferred embodiments of a method of identifying critical points of the continuous relative density using eigenvector following, and a method of associating critical points with one another by following a gradient path of the continuous relative density between the critical points, are discussed in Example 3.

Application of the principles of the preferred embodiment to the analysis of data from computational fluid dynamics is described in Example 4.

Application of the principles of the preferred embodiment to the study of reactions and folding of proteins is described in Example 5.

Application of the principles of the preferred embodiment to edge detection in graphical images is described in Example 6.

Application of the principles of the preferred embodiment to alternative visualization of higher dimensional scalar fields is described in Example 7.

Application of the principles of the preferred embodiment to the analysis of data in the financial industry is described in Example 8.

Identification of the computer program MORPHY is provided in Example 9.

Source code for a computer program used in a preferred embodiment of the present invention is provided in Example 10.

Source code for a computer program used in a more preferred embodiment of the present invention is provided in Example 11.

EXAMPLE 1

This example relates to the application of image reconstruction processes to protein crystals.

Associated with interpretation of protein images is the ability to locate and identify meaningful features of a protein structure at multiple levels of resolution. This requires a simplified representation of a protein structure, one that preserves relevant shape, connectivity and distance information. In the present approach, molecular scenes are represented as 3D annotated graphs, which correspond to a trace of the main and side chains of the protein structure. The methodology has been applied to ideal and experimental electron density maps at medium resolution. For such images, the nodes of the graph correspond to amino add residues and the edges correspond to bond interactions. Initial experiments using low-resolution electron density maps demonstrate that the image can be segmented into protein and solvent regions. At medium resolution the protein region can be further segmented into main and side chains and into individual residues along the main chain.

Furthermore, the derived graph representation of the protein can be analyzed to determine secondary structure motifs within the protein.

Protein Structure

Since the 3D topology of a protein cannot as yet be predicted from its known amino acid sequence alone, the experimental techniques of X-ray crystallography and nuclear magnetic resonance currently provide the only realistic routes for structure determination. A computational approach for the analysis of protein images generated from crystallographic data is set forth below.

Scene Analysis

A crystallographic experiment yields data that define a 3D function, which allows for the construction of a 3D array of voxels of arbitrary size. An interpretation of the 3D atomic arrangement in a crystal structure is readily available for small molecules using the data generated from X-ray diffraction techniques. Given the magnitudes of the diffracted waves and prior knowledge about the physical behavior of electron density distributions, probability theory can be applied to retrieve phase information. Once magnitudes and phases are known, the spatial arrangement of atoms within the crystal can be obtained by a Fourier transform. The electron density function that is obtained, $\rho(x,y,z)$, is a scalar field visualized as a 3D grid of real values called the electron density map. High-density points in this image are associated with the atoms in the small molecule.

The construction of an interpretable 3D image for a protein structure from diffraction data is significantly more complex than for small molecules, primarily due to the nature of the phase problem, it generally involves many iterations of calculation, map interpretation and model building. It also relies extensively on input from an expert crystallographer. It has previously been proposed that this process could be enhanced through a strategy that integrates research in crystallography and artificial intelligence and rephrases the problem as a hierarchical and iterative scene analysis exercise (Fortier, S. et al. (1993) Molecular scene analysis: The integration of direct methods and artificial intelligence strategies for solving protein crystal structures. *Acta Crystallographica,* D49:168–178; Glasgow, J. et al. (1993) Molecular scene analysis: crystal structure determination through imagery. In Hunter, L. (Ed.), *Artificial Intelligence and Molecular Biology,* pp. 433–458. AAAI Press, Menlo Park, Calif.). The goal of such an exercise is to reconstruct and interpret images of a protein at progressively higher resolution. For an initial low-resolution map, where the protein appears as a simple object outlined by its molecular envelope, the goal is to locate and identify protein and solvent regions. At medium-resolution, the goal involves locating amino acid residues along the main chain and identifying secondary structure motifs. At higher resolution, the analysis would attend to the identification of residues and, possibly, the location of individual atoms.

A primary step in any scene analysis (whether vision, medical or crystallographic data are used) is to automatically partition an image representation into disjoint regions. Ideally, each segmented region corresponds to a semantically meaningful component or object in the scene. These parts can then be used as input to a high-level classification task. The processes of segmentation and classification may be interwoven; domain knowledge, in the form of a partial interpretation, is often useful for assessing and guiding further segmentation.

Several approaches to image segmentation and classification have been considered in the vision literature. Of particular interest for the molecular domain is an approach described by Besl, P. et al. (1986) (Invariant surface characteristics for 3D object recognition in range images. *CVGIP,* 33:33–80), where the surface curvature and sign of a Gaussian is derived for each point on the surface of a range image. Image segmentation is then achieved through the identification of primitive critical points (peaks, pits, ridges, etc.). Haralick, R. et al. (1983) (The topographic primal sketch, *International Journal of Robotics Research,* 2:50–72) defined a similar set of topographic features for use in 2D image analysis; Wang, L. et al. (1993) (Direct gray scale extraction of features for character recognition. *IEEE Trans. Patt. Anal. Mach. Intell.,* PAMI-15(10):1053–1067), and later Lee, S. et al. (1995) (Direct extraction of topographic features for gray scale character recognition. *IEEE Trans. Patt. Anal. Mach. Intell.,* PAMI-17(7):724–729), extended this work to extract features for character recognition. Gauch, J. et al. (1993) (Multiresolution analysis of ridges and valleys in grey-scale images. *IEEE Transactions on Pattern Analysis and Machine Intelligence,* PAMI-15(6): 635–646) also identify ridge and valley bottoms in 2D images, where a ridge is defined as a point where the intensity falls off sharply in two directions and a valley bottom is a point where the intensity increases sharply in two directions. They further examined the behavior of the ridges and valleys through scale space; the resulting resolution hierarchies could be used to guide segmentation. Maintz, J. et al. (1996) (Evaluation of ridge seeking operators for multimodality medical image matching. *IEEE Transactions on Pattern Analysis and Machine Intelligence,* 18(4): 353–365) and Guziec, A. et al. (1992) (Smoothing and matching of 3-d space curves. *Visualization in Biomedical Computing, Proc. SPIE,* 1808:259–273) use 3D differential operators through scale space to define ridges and troughs. These provide landmarks which can be used to register images. Leonardis, A. et al. (1995) (Segmentation of range images as the search for geometric parametric models. *International Journal of Computer Vision,* 14:253–277) use an approach where surface fitting (using iterative regression) and volume fitting (model recovery) are initiated independently; the local-to-global surface fitting is used to guide multiple global-to-local volume fittings, and is used in the evaluation of possible models.

As will be discussed in the next section, a topological approach is being used for the segmentation and classification of molecular scenes. Similar to the method of Gauch et al. (1993), critical points are used to delineate a skeletal image of a protein and segment it into meaningful parts. These critical points are considered in the analysis of the segmented parts. This approach can also be compared to a skeletonization method, which has been described by Hilditch, C. J. (1969) (Linear skeletons from square cupboards. *Machine Intelligence,* 4:403–420) and applied in protein crystallography by Greer, J. (1974) (Three-dimensional pattern recognition: An approach to automated interpretation of electron density maps of proteins, *Journal of Molecular Biology,* 82:279–301). Unlike Greer's algorithm, which "thins" an electron density map to form a skeleton that traces the main and secondary chains of the molecule, our proposed representation preserves the original volumetric shape information by retaining the curvatures of electron density at the critical points. Furthermore, rather than thinning electron density to form a skeleton, our approach reconstructs the backbone of a protein by connecting critical points into a 3D graph structure.

Critical points in an image have also been considered in the medical domain. Higgins, W. et at. (1996) (System for analyzing high-resolution three-dimensional coronary anglograms. *IEEE Transactions on Medical Imaging*, 15(3): 377–385) analyze coronary anglograms from CT data by thresholding to define "bright" regions that correspond to the area around peak critical points. These seed regions are then grown along ridges until there is a steep dropoff. Postprocessing removes cavities and spurs. The resulting volume is a tree-like structure, which is then skeletonized and further pruned to provide axes. The axes are converted to sets of line segments with some minimum length. This is similar to BONES (Jones, T. et al. (1991) (improved methods for building protein models in electron-density maps and the location of errors in those models. *Acta Crystallographica*, A47:110–119), a graphical method which has been developed and applied to the interpretation of medium- to high-resolution protein maps. This method incorporates a thinning algorithm and postprocessing analysis for electron density maps. Also worth mentioning is a previously described methodology for outlining the envelope of a protein molecule in its crystallographic environment (Wang, B. (1985) Resolution of phase ambiguity in macromolecular crystallography. In: Wyckoff, H., Hirs, C., & Timasheff, S. (Eds.), *Diffraction Methods for Biological Macromolecules*, Academic Press, New York).

A distinct advantage of molecular scene analysis, over many applications in machine vision, is the regularity of chemical structures and the availability of previously determined molecules in the Protein Data Bank (PDB) (Bernstein, F. et al. (1977) The Protein Data Bank: A computer-based archival file for macromolecular structures. *Journal of Molecular Biology*, 112:535–542). This database of 3D structures forms the basis of a comprehensive knowledge base for template building and pattern recognition in molecular scene analysis (Conklin, D. et al. (1993) Representation for discovery of protein motifs. In: Hunter, L., Searls, D., & Shavlik, J. (Eds), *Proceedings of the First International Conference on Intelligent Systems for Molecular Biology*, AAAI/MIT Press, Menlo Park, Calif.; Hunter, L. et al. (1991) Applying Bayesian classification to protein structure. In: *Proceedings of the Seventh IEEE Conference on Artificial Intelligence Applications*, Miami, Fla.; Unger, R. et al. (1989) A 3D building blocks approach to analyzing and predicting structure of proteins, *Proteins*, 5:355–373); although the scenes we wish to analyze are novel, their substructures most likely have appeared in previously determined structures. Another significant difference between molecular and visual scene analysis is that diffraction data resulting from protein experiments yield 3D images, simplifying or eliminating many of the problems faced in low-level vision (e.g., occlusion, shading). The complexity that does exist in the crystallographic domain relates to the incompleteness of data due to the phase problem.

Segmentation and Interpretation of Protein Images

A topological approach to the representation and analysis of protein electron density maps was implemented in a program called ORCRIT (Johnson, C. (1977). ORCRIT. The Oak Ridge critical point network program. Tech. Rep., Chemistry Division, Oak Ridge National Laboratory, USA). Recent studies suggest that this approach can also be applied to the segmentation of medium-resolution protein images (Leherte, L. et al. (1994) A computational approach to the topological analysis of protein structures. In: Altman, R. et al. (Eds.), *Proceedings of the Second International Conference on Intelligent Systems for Molecular Biology*. MIT/AAAI Press, Menlo Park, Calif.). In this section we describe such a topological approach for the analysis of low and medium-resolution electron density maps of proteins.

The information stored in an electron density map for a protein may be represented and analyzed at various levels of detail (see FIG. 1). Resolution in the electron density images of proteins is often measured in terms of angstrom units (Ang). At high-resolution (FIG. 1(*a*)) individual atoms are observable; at medium-resolution (FIG. 1(*b*)) atoms are not observable, but it is possible to differentiate the backbone of the protein from its side chains, and secondary structure motifs may be discernable. A clear segmentation between the protein molecular envelope (region in which the atoms of the protein reside) and the surrounding solvent region can still be seen at low-resolution (FIG. 1(*c*)).

Methods from both machine vision and crystallography were considered in the development of our computational approach to the analysis of protein structures. Among those studied, a topological analysis provided the most natural way to catch the fluctuations of the density function in the molecular image. This section is an overview of such a method for mapping a 3D electron density map onto a graph that traces the backbone of the protein structure. The results of applying the method for the segmentation of low and medium-resolution maps of protein structures reconstructed using the Protein Databank of Brookhaven are also presented. As well, it is shown how critical point graphs constructed for medium resolution maps can be further analyzed in order to identify alpha-helix and beta-sheet substructures.

Representation of Protein Structure

Crucial to a molecular scene analysis is a representation that will capture molecular shape and structure information at varying levels of resolution; an important step in a molecular scene analysis is the parsing of a protein, or protein fragments, into shape primitives so as to allow for their rapid and accurate identification. Shape information can be extracted from several depictive representations—for example, van der Waals surfaces, electrostatic potentials or electron density distributions. Since molecular scene analysis is primarily concerned with images reconstructed from crystallographic experiments, electron density maps provide a natural and convenient choice for the input representation.

An electron density map is depicted as a 3D array of real, non-negative values corresponding to approximations of the electron density distribution at points in the unit cell of a crystal. For the task of segmenting this map into meaningful parts, we also consider the array in terms of a smooth and continuous function $\rho$, which maps an integer vector $r=(x, y, z)$ to a value corresponding to the electron density at location r in the electron density map. Similar to related formalisms in vision (the level of representation of the electron density map is comparable to a 3D version of the primal sketch in (Marr, D. et al. (1978) Representation and recognition of the spatial organization of three-dimensional shapes, *Proceedings of the Royal Society of London*, B200:269–294), the information in an electron density map is uninterpreted and at too detailed a level to allow for rapid computational analysis. Thus, it is essential to transform this array representation into a simpler form that captures the relevant shape information and discards unnecessary and distracting details. The desired representation should satisfy the three criteria put forward by Marr, D. et al. (1978) concerning: 1) accessibility—the representation should be derivable from the initial electron density map at reasonable computing costs; 2) scope and uniqueness—the representation should provide a unique description of all possible molecular shapes at varying levels of resolution; and 3) stability and sensitivity—the representation should capture the more general (less variant) properties of molecular shapes, along with their finer distinctions.

Several models for the representation and segmentation of protein structures were considered. These included a generalized cylinder model (Binford; T. (1971) Visual perception by a computer, In: *Proceedings of IEEE Conference on Systems and Control* Miami, Fla.), and a skeletonization method (Greer, J. (1974). Three-dimensional pattern recognition: An approach to automated interpretation of electron density maps of proteins, *Journal of Molecular Biology*, 82:279–301; Hilditch, C. J. (1969) Linear skeletons from square cupboards, *Machine Intelligence*, 4:403–420). We chose a topological approach, which has been previously applied in both chemistry and machine vision. In chemistry, the approach has proven useful for characterizing the shape properties of the electron density distribution through the location and attributes of its critical points) (points where the gradient of the electron density is equal to zero) (Johnson, C. (1977) ORCRIT The Oak Ridge critical point network program, Tech. Rep., Chemistry Division, Oak Ridge National Laboratory, USA).

In the following section, we describe the representation of a protein structure in terms of a set of critical points obtained through a topological analysis.

Deriving Critical Point Graphs

In the topological approach to protein image interpretation, a protein is segmented into its meaningful parts through the location and identification of the points in the electron density map where the gradients vanish (zero-crossings or critical points). At such points, local maxima and minima are defined by computing second derivatives which adopt negative or positive values respectively. The first derivatives of the electron density function ρ characterize the critical points, and the second derivatives provide information on the critical points; in particular, they identify the type of critical points for the map. For each index value r=(x,y,z) in the electron density map, we define a function ρ.

Candidate grid points (those that are a maximum or a minimum along three mutually orthogonal axes) are chosen and the function ρ is evaluated in their vicinity by determining three polynomials (one along each of the axes) using a least square fitting. ρ is the tensor product of these three polynomials. The location of a critical point is derived using the first derivative of ρ. The second derivatives are used to determine the nature of the critical point For each critical point, we construct a Hessian matrix:

$$H(r) = \begin{vmatrix} \partial^2 \rho / \partial x^2 & \partial^2 \rho / \partial x \partial y & \partial^2 \rho / \partial x \partial z \\ \partial^2 \rho / \partial y \partial x & \partial^2 \rho / \partial y^2 & \partial^2 \rho / \partial y \partial z \\ \partial^2 \rho / \partial z \partial x & \partial^2 \rho / \partial z \partial y & \partial^2 \rho / \partial z^2 \end{vmatrix}$$

This matrix is then put in a diagonal form in which three principal second derivatives are computed for the index value r:

$$H'(r) = \begin{vmatrix} \partial^2 \rho / \partial (x')^2 & 0 & 0 \\ 0 & \partial^2 \rho / \partial (y')^2 & 0 \\ 0 & 0 & \partial^2 \rho / \partial (z')^2 \end{vmatrix}$$

Figure 2:
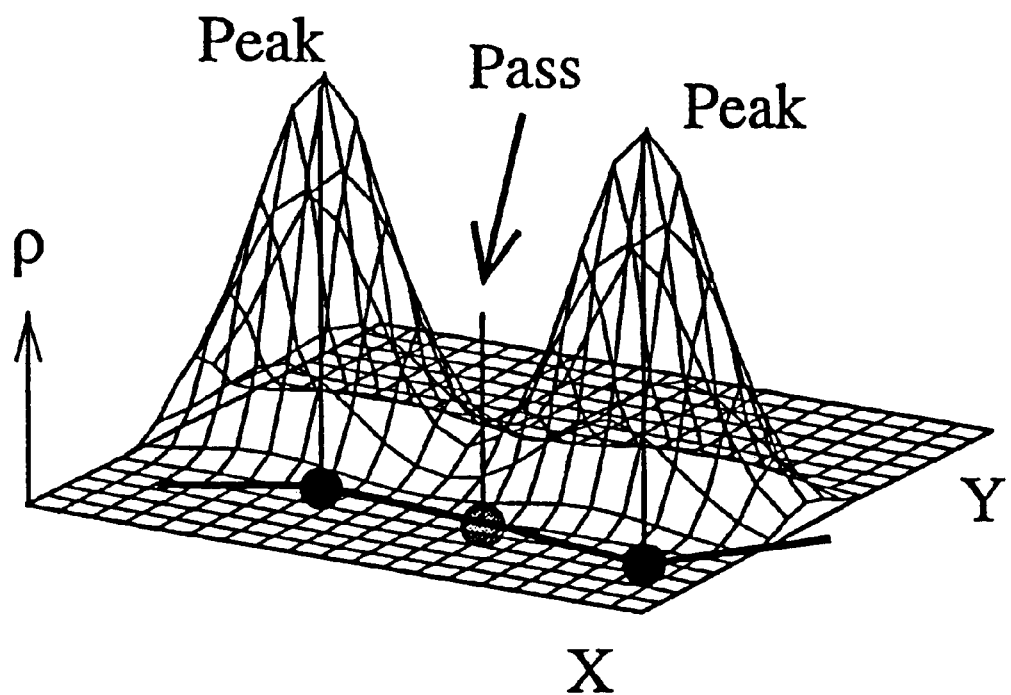
FIG. 2 is a graphical illustration of critical points in two dimensions (x and y) plotted against density function $\rho$.

The three non-zero diagonal elements of array H'(r)—the eigenvalues—are used to determine the type of critical points of the electron density map. Four possible cases are considered depending upon the number of negative eigenvalues, $n_E$. When $n_E=3$, the critical point r corresponds to a local maximum or peak; a point where $n_E=2$ is a saddle point or pass. $n_E=1$ corresponds to a saddle point or pale, while $n_E=0$ characterizes r as a pit. FIG. 2 depicts a 2D graphical projection of potential critical points.

High density peaks and passes are the only critical points currently being considered in our study. Low density critical points are less significant since they are often indistinguishable from noise in experimental data.

The use of the critical point mapping as a method for analyzing protein electron density maps was first proposed by Johnson (1977) for the analysis of medium to high-resolution protein electron density maps. Within the framework of the molecular scene analysis project, the use of critical points is being extended for the analysis of medium and low-resolution maps of proteins. The topological approach to the segmentation of proteins was initially implemented by Johnson in the computer program ORCRIT (Johnson, 1977). By first locating and then connecting the critical points, this program generates a representation that captures the skeleton and the volumetric features of a protein image. The occurrence probability of a connection between two critical points i and j is determined by following the density gradient vector. For each pair of critical points, the program calculates a weight $w_0$ which is inversely proportional to the occurrence probability of the connection. The collection of critical points and their linkage is represented as a set of minimal spanning trees (connected acyclic graphs of minimal weight).

EXAMPLE 2

Modelling electron density maps is an important step in the analysis of protein crystallographic data. Since the electron densities are only provided in a discrete array, there is much information (density values off the grid, derivative information, etc.) that is not directly available, but that does exist, since the underlying electron density is a smooth function. By applying an interpolation model with appropriate characteristics, we can approximate the underlying electron density function and regain some of the lost information. The preferred principal characteristics we want in our interpolant are robustness and smoothness; however, there are techiques as will be recognized by those skilled in the art for using interpolants that are not entirely robust or smooth. The benefit of robustness is clear. The benefit of smoothness comes from the type of information we wish to extract from the electron density function after the interpolation.

Modelling Density Maps with Splines

A global interpolation technique, and one that has been shown to be robust in many applications (De Boor, C. (1978) A practical guide to splines, *Applied Mathematical Sciences*, Vol. 27, Springer-Verlag), is the modelling of density maps using polynomial splines. In their simplest, one-dimensional form splines join a sequence of points together with short polynomial segments. The key to their smoothness is that at the joining of two segments (a knot, in spline terminology), not only must the curves be continuous, but so must their first n derivatives. For most applications, including this one, cubic splines are used because they provide continuity in both the first and second derivative across the entire function. This continuity provides advantages because the second derivative information is used extensively in the eigenvector following method of critical point searching.

Implementation

One mode of interpolation has been performed by the inventors on a density grid that contains the asymmetric unit and between 2 and 5 grid elements beyond the asymmetric unit. This buffer minimizes the edge effects of the spline interpolation inside the asymmetric unit interpolants are fully described by an array of basis spline coefficients. These coefficients of the interpolating spline are related to the grid density values through linear relationships. This means that, given the grid density values, the basis spline coefficients are determinable by solving a number of linear systems (De Boor, 1978). We have been using Numerical Recipes' (Press, W. H., et al. (1994) *Numerical recipes in C*, Cambridge University Press, second edition) linear algebra functions to solve these linear systems.

Once the basis spline coefficients have been determined, it is a simple matter to define functions that use the coefficients to calculate the interpolated density, gradient (first derivatives) and Hessian (matrix of second derivatives) of the interpolant.

Fourier Spline Technique

Another interpolation scheme which has been applied by the inventors to crystallographic data is a technique pioneered by Eric Gosse (1980) (Approximation and optimization of electron density maps, Ph.D. Dissertation, Stanford University, Department of Computer Science). Grosse refers to it as spectral spline interpolation. Spectral splines differ from interpolating spines in that they do not generate a function that interpolates between the data points. Instead, the splines act as a form of function fitting, where the splines have the same Fourier series expansion as some original, periodic, function (up to a certain precision).

For the crystallographic domain, there are some obvious advantages to using the spectral spline interpolation rather than the standard algebraic interpolation, which is what has previously been used. Not the least among these is the fact that the spectral splines take into account the periodicity of the crystal structure with no extra computational expense. It would be very cumbersome, computationally, to expand the algebraically generated splines to properly model the entire crystal structure.

There is a second significant advantage to the use of Fourier techniques, which is that the electron density map itself is generated from a Fourier series expansion of the structure factors of the crystal. This means that the original input data, structure factor magnitude, and phase is already in the frequency domain, and that to calculate the spectral spline coefficients for the crystal is only slightly more expensive to calculate than the electron density map. Determining the spline coefficients in this manner also removes some of the error introduced by expanding the Fourier series, sampling it discretely and then applying the algebraic spline interpolation. The spectral splines provide a leaner, more elegant solution to the interpolation problem for crystallographic data.

EXAMPLE 3

This example illustrates the Eigenvector following method and the gradient path following method for chain determination in low resolution X-ray studies of proteins.

Background re Eigenvector Following in Known Structures

The searching algorithms utilized for many years in topological studies of isolated atoms and complexes were based on the Newton-Raphson method. The Newton-Raphson method departs from a truncated Taylor expansion at a point $x=x_0+h$ about $x_0$ of a multidimensional scalar function:

$$\rho = \rho_0 + g^T h + (\tfrac{1}{2}) h^T H h \tag{1}$$

where $\rho$—charge density g—gradient of k at $x_0$

H—Hessian matrix at $x_0$ h—the step

In the Newton-Raphson search, h, is $$h = -H^{-1}g \tag{2}$$

which can be written in terms of the eigenvectors, $V_i$, and eigenvalues, $b_i$, of the Hessian:

$$h = -\Sigma F_i V_i / b_i \text{ (for } i=1 \text{ to 3)} \tag{3}$$

where $$F_1 = V_i^T g \tag{4}$$

$$= \sum V(j,i)^* g(j) \text{(for } j = 1 \text{ to 3)}$$

is the projection of the gradient g along the local eigenmode $V_i$.

The weakness of this searching algorithm is that you must have a good starting point That is, should you wish to search for a peak (a maximum in the scalar function $\rho$), but your starting point is in a region where the Hessian has two positive eigenvalues, the step will not necessarily put the next point closer to the desired peak. In other words, when exploring the topology of a system, having found a particular critical point, you then need to step away towards another with the desired signature.

The Eigenvector following method, initially applied to locate transition states on energy surfaces, has been modified for the general exploration of potential surfaces and also applied to the exploration of the topology of the charge density of isolated molecules and complexes. Building on earlier work by Cerjan, C. J. et al. (1981) (On finding transition states, *J. Chem. Phys.* 25:2800–2803), Simons, J. et al. (1983) (Walking on potential energy surfaces, *J. Phys. Chem.* 87:2745–2753), Banerjee, A. et al. (1985) (Search for stationary points on surfaces, *J. Phys. Chem.* 89:52–55), and Baker, J. (1986) (An algorithm for the location of transition states, *J. Comput. Chem.* 7:385–389) who explored energy surfaces, Popelier, P. L. A. (1994) (A robust algorithm to locate automatically all types of critical points in the charge density and its laplacian, *Chem. Phys. Lett.*, 228:160–164) applied the method to the examination of the charge density. In short, equation 3 has the term $b_i$ modified to be $$b_i - \lambda$$

where $\lambda$ is called the shift parameter. Furthermore, as pointed out by Banerjee et al. (1985) this can be further modified utilizing 2 shift parameters, one for modes relative to which $\rho$ is to be maximized, $\lambda_\rho$, and one for modes for which it is to be minimized, $\lambda_n$. $\lambda_\rho$ is identified as the highest eigenvalue of the respective set of solutions while $\lambda_n$ is the lowest. The resulting set of eigenvalue equations corresponding to each type of critical point (rank 3) are given in Table 1 of Popelier's (1994) report.

The eigenvector following method was used by Popelier to examine densities obtained from quantum mechanical calculations on isolated systems.

Application of the Eigenvector Following Method to Unknown Structures of Substances Solving protein structures from low resolution X-ray crystallographic data has been problematic to date. The Molecular Scene Analysis Group at Queen's University has been applying many techniques available from the fields of Chemistry, Physics and Computing Science for some time to facilitate the elucidation of these protein structures. The application of elements of topology as utilized by Bader, R. F. W. (1990) (*Atoms in Molecules: A Quantum Theory,*

Clarendon Press, Oxford, pp. 16–20) to this problem has shown promise but lacked a certain exactness. At low resolution, peptide fragments appear as blobs of density with very little apparent structure. The implementation of the eigenvector following method during the examination of the topology of the density facilitates the location of all critical points and allowing the tracing of the connections between the peaks in the density (peptide fragments) to be traced. The tracing of the connections between peptide blobs (fragments) is accomplished by tracing the gradient paths from the passes to the associated peaks. The result is a complete description of the peptide chain and a wealth of information regarding its makeup or composition.

In this application, eigenvector following is applied to densities for solid state substances obtained from experiment. The experimental densities are modelled using cubic splines, allowing the calculation of analytical first and second derivatives.

Two embodiments of computer software source code for an exemplary application of interpolating employing cubic splining, eigenvector following and gradient path following to proteins are set forth in Examples 10 and 11. The input to the source code is a separately provided file containing cubic spline coefficients that have been fit to an experimental relative density grid and generated as discussed in Example 2. The source code is a combination of C code and Fortran.

Note that should some other continuous set of functions be chosen (rather than cubic splines) then those coefficients and appropriate routines would have to be adapted correspondingly. The cubic spline routines necessary to calculate the values of the density and $1^{st}$- and $2^{nd}$-derivatives have been provided with the source code. Other input would be contained in a file with the extension 'inp' and follows the MORPHY (see below) genre with the addition of a section 'GRID' which gives the information for generation of the grid for the initial search for peaks. This is up to the user to define and would have the form '27 36 43' and is in grid units. The next line contains a number giving the stepsize or spacing for the grid generation. Also, at present, the program requires interactive input of:

1) file name for the input (fn.inp)
2) the dimensions of the splining coefficients (eg 40 41 36)
3) the file name that contains the coefficients.

The source code in Example 10 has been adapted from a program known as MORPHY which implements the Popelier methods as described in the Popelier (1994) report. The original MORPHY source code is currently available as set out in Example 9.

The source code in Example 11, MORDEN, is a more efficient embodiment of the source code listed in Example 10.

While the embodiments set forth in Examples 10 and 11 are specifically adapted for the analysis of 3-dimensional structures, particularly those of proteins, individuals skilled in the art will recognize that these embodiments may be modified in accordance with the principles described herein so as to extend their applicability to systems and spaces having any number of dimensions. Examples of such other analyses to which the present invention is applicable are provided below in Examples 4 to 8.

MORPHY Background

The program MORPHY performs an automated topological analysis of a molecular electron density given a wavefunction file for the system in question. This wavefunction would consist of atomic coordinates, a wavefunction obtained from a quantum mechanical calculation, exponents for the Gaussian functions the wavefunction is expressed in (the basis set) and the centre assignments for those Gaussian functions.

Protein Structure Analysis Source Code

The protein structure problem is that we have neither a wavefunction nor the atomic coordinates. What information we have comes from X-ray experiments that can be transformed into an electron density map whose detail depends on the resolution of the X-ray measurements. The program has been altered to reflect this reality and to utilize the information we have. The following paragraph summarizes those alterations.

Generation of Data Through Cubic Splining and Required Adaptations

The 3-dimensional density map for the unit cell has been modelled using cubic splines. This set of cubic splines and their coefficients now form our equivalent basis set and "wavefunction". The routines that utilize the splining coefficients to calculate the density, first and second derivatives are in the C programming language and thus an interface from the FORTRAN code to these routines has been implemented. The routines INPUTWAVE, MO0 through MO01234, RHOONE, RHOTWO, RHOTHREE, RHO-FOUR and RHOZERO and calls to them have been deleted. Calls to these routines have been replaced with appropriate calls to the interface and subsequent C routines.

As no nuclear coordinates are input, the automated searching algorithm which utilizes these to search for other types of critical points has been altered to initially conduct a grid search for maxima, peaks, in the density and then proceed with the automatic search. All reference to nuclear coordinates have been eliminated and replaced with the coordinates of the peaks found through this search. This is a key alteration in the program as most calculations (DO loops, etc.) are referenced to the number of nuclei and their coordinates. Other changes involve parameters such as convergence criteria (e.g., definition of a zero gradient=$1\times10^{-10}$) and redimensioning arrays to appropriate values through the parameters common block to suit the size of each system. Note that dimensions dependent on the maximum number of nuclei must be replaced with the maximum number of peaks.

MORDEN Background

Sharing a similar background with MORPHY, MORDEN has been written specifically to perform an automated topological analysis of 3D density. In the form provided, it utilizes cubic splines that model the 3D density map for a regular volume such a unit cell. The routines that utilize the splining coefficients to calculate the density first and second derivatives are in the C programming language. The remainder of the routines are in FORTRAN.

EXAMPLE 4

Application of the Principles Described Herein to the Analysis of Data from Computational Fluid Dynamics Of interest to a number of industries is the flow of fluids (gases, water or some other fluid) over surfaces, or the development of the mixing and reaction of the fluids exiting some orifice such as a burner in a furnace. There are many factors which can inhibit desired behaviour such as smooth flow over an aircrafts wing or the complete combustion in the desired location of mixing gases. The ability to follow the various processes and understand how and why certain behaviours are exhibited is one of the problems in Computational Fluid Dynamics (CFD).

There are a variety of properties that one might measure in a CFD experiment such as concentrations of reactants, heat or pressure as a function of position (3D) and, as these are dynamic systems, time (4D). In a combustion reaction, such as in a furnace or turbine, the concentrations of various reactants and products would change as the reaction proceeds and the mixtures position is displaced with time. It would be desirable to design a burner with stability and a predictable structure in the combustion process to maximize the heat or thrust generated.

A sequential series of snapshots of the desired property over the volume under study would enable the fitting of spline functions to give a continuous function for the desired property for each snapshot. This would enable the application of the eigenvector following and gradient path following techniques described herein to elucidate the topological structure of the system for each snapshot. Additionally, it is the topological development in time of the reaction/mixing that gives the stability of the system. Thus, utilizing 4-dimensional splines to model the 3-dimensional coordinates and time allows the topological analysis to be carried out in 4 dimensions.

Steps involved in applying the principles described herein to analysis of CFD data include:
1) Obtain experimental or modelled data and use methods known in the art to transform collected data into discrete 3- and 4-dimensional arrays for the desired property (e.g., temperature).
2) Fit 3- and 4-dimensional spline functions to the respective arrays to give a continuous function for each array.
3) Employ eigenvector following on the spline functions, and associate critical points by following a gradient path of the functions between the critical points.
4) Direct the output to a desired method of presentation or for further analysis to discover additional relationships.

EXAMPLE 5
Application of the Principles Described Herein to the Study of Reactions and Folding of Proteins The study of reactions and the folding of proteins is of immense interest to the pharmaceutical industry. The understanding of reaction mechanisms and how proteins fold to give 3-dimensional structures would give great insight into areas such a drug design. See, for example, Bader, R. F. W. et al. (1982) (*J. Am. Chem. Soc.* 104:940–945). Techniques, such as high-speed X-ray experiments, are now making data available, although at low resolution, that invites the application of the methodology described herein for an understanding of the processes from a topological perspective.

The methodology described herein is being employed to help elucidate the 3-dimensional structure of proteins from low resolution X-ray crystallographic data. This data is a time average, thus giving a static system for analysis. The data obtained from high-speed X-ray experimental studies of reactions involving proteins may be treated in an analogous fashion for each time slice.

Thus, according to the principles described herein, the topology of a 3-dimensional volume is modelled and analysed to elucidate the 3-D structure of the protein at that point. To further understand these dynamic processes; however, a fourth dimension, time, must be included. This means that spline functions must be fit to the 4-D array representing the 3-D slices of the structure of the protein (and/or reactants) at each point in time.

Steps involved in applying the current invention to the study of protein reactions or protein folding:
1) Obtain experimental or modelled data and use methods known in the art to transform collected data into discrete 3- and 4-dimensional arrays for the desired property.
2) Fit the 3- and 4-dimensional spline functions to the respective arrays to give a continuous function for each array.
3) Employ eigenvector following on the spline functions, and associate critical points by following a gradient path of the functions between the critical points.
4) Direct the output to a desired method of presentation or for further analysis to discover additional relationships.

EXAMPLE 6
Application of the Principles Described Herein to Edge Detection in Graphical Images Most graphical images (including presentation of output for methods previously described herein) are represented in computers as arrays of colour values, which are easily translated into an image on a computer screen. These images may be any images generated by technologies relating to satellite surveillance, medical imaging technology, digital cameras, inspection of manufactured goods, and the like. The ability to use computers to automatically interpret images is becoming more and more important, e.g., to automatically detect military installations in satellite images, tumours in medical images, facial recognition in security camera images.

The proposed method has particular applications in sequential edge detection in such graphical images, or the tracing of a path through an edge image, or gradient image. Edge detection is a fundamental pre-processing step required for image interpretation. In an edge image, each pixel represents some measure of the local colour change in the neighbourhood of the corresponding pixel in the original image. Edge detection is a process that translates the image from an array of colours to a set of line segments representing the borders or edges between objects in the image. These edges are then spliced together to make up the outline of objects that can be recognized automatically; i.e., a single path is found through the edge image. For example, this path can correspond to the outline of any object that can be recognized automatically, the meeting of two pieces of metal in an automated welding operation, or to traces on a printed circuit board.

Conventional approaches to creating paths through the image graph involve choosing a starting pixel, applying a decision algorithm to determine the next pixel in the path, and applying another decision algorithm to determine when the end point of the path has been reached. Steps involved in applying the methods of the principles described herein to edge detection include:
1) Obtain an image in array format from some source. For non-array images (photographs, X-ray slides, etc), apply digital scanning techniques to generate such a version of the image.
2) From the image generate a gradient image, or an image representing rates of change of colour, using methods known in the art.
3) Generate spline coefficients for the gradient image.
4) Employ eigenvector following to identify critical points, and associate critical points by following a gradient path between critical points.
5) Direct the discovered peak/pass graph to a graphical viewer or printer, or
   a) edge detection/recognition system (military hardware recognition, facial recognition);
   b) a volume determination system (determining foetal volumes, tumour volumes); and
   c) a post-processing module to improve the edges.

Application of the methods of the invention to edge detection provides several advantages over the current methodology. Firstly, the number of decision points is reduced. The number of peaks in the edge image is far fewer than the number of pixels, and, particularly, there are fewer peaks than pixels along the path to be traced. As a result, decision algorithms need to be applied less frequently, therefore reducing the probability of error before the end of the path is reached.

Secondly, the methods of the invention provide non-local information for choosing a path out of a peak. The pass high is indicative of the lowest edge value along the way to an adjacent peak. This is a much more useful measure of edge quality than the edge value at a single adjacent pixel of conventional techniques, because it includes an entire section of the path, removing the risk of forming dead-ends.

Thirdly, the peak/pass structure according to the method of the invention is much thinner than the edge image, as it is comprised of a series of points and edges. In a conventional image with a thick edge, determining a path is difficult, as the algorithm will wander within pixels with high edge values. In contrast, the peak/pass structure of the principles described herein selects the highest edge values and forces direct connectivity between the peaks, eliminating any wandering paths.

EXAMPLE 7
Application of the Principles Described Herein to Alternative Visualization of Higher Dimensional Scalar Fields Scalar fields exist in every field of science (fluid dynamics, stress analysis, quantum physics, physical chemistry, geography, geology, etc.) and many of them are in 2 or 3 or higher number of dimensions. Visualizing even a 3 dimensional scalar field is difficult only possible by taking cross-sections of the field or generating contour volumes. In all cases, it would be easier to visualize a vector-based representation of the data, if it still contained the important information. In many of these fields, the information of interest is partially contained in the locations of the points where the scalar field represents a maxima (or minima). Reducing the scalar field to the set of extremal points makes it possible to visualize the data more easily (projecting points onto a computer screen, for instance) but most of the information contained in the scalar field is no longer present. For applications where the relationships between the extremal points is of interest, the principles described herein can be applied successfully to generate an easily visualized graph structure that contains both the extremal points (as vertices) as well as more information about the underlying scalar field (in the peak/pass graph structure). The meaning of the relationship between the extremal values is domain specific: chemical bonds in quantum chemical models, ridges of erosion danger in water flow measurements, veins of ore in geological sample data, stress bands in civil engineering applications, etc. These visualizations are more easily seen, because they do not fill the space, and they can lead to new insights because they show structure of the scalar field that might not be apparent when looking directly at the field itself.

Steps involved in applying the principles described herein to an alternative visualization of higher dimensional scalar fields include:

1) Model the scalar field with some mathematical function (splines, solutions to partial differential equation models, ad-hoc function definition).
2) Employ eigenvector following on the functions to determine extremal (critical) points and associate extremal points by following a gradient path between the extremal points on the scalar field.
3) Direct the discovered extremal values and the associated graph structure to a graphical viewer or printer. For data in higher than 3 dimensions, a projection of the data can be displayed, or presented using some method known in the art of graphical display.

EXAMPLE 8
Application of the Principles Described Herein to the Analysis of Data in the Financial Industry In the financial industry, the majority of bankers, treasurers and investors work with 2D representations although interactive 3D visualization is more effective. Chorafas, D. N. (1998) (The market risk amendment, McGraw-Hill, Toronto) has stated "Even three dimensions can be inadequate because many problems confronting us in finance are n-dimensional, with n a lower two-digit number." Much of the banking industry has moved to a six-dimensional structure, and fine-grain approaches utilizing as many as 23 dimensions may be used. Such multi-dimensional analyses represent much greater complexity.

The use of modem technology increases the efficiency of the financial system but it also increases the complexity of the system and thus the exposure to risk which must be managed. The increased pace of data sampling, which is moving from daily (e.g., high and low valuations) to minute by minute, results in an increasingly larger data set which must be analyzed for the complex multivariable relationships that give insight into the direction of various markets and permit assessment of risks associated therewith.

The financial markets, although complex, represent dynamic systems moving from highs, lows and saddle points. There are periods where there is equilibrium and change. The application of the principles described herein would mimic the analysis of multi-dimensional energy surfaces, the study of which led to the development of the eigenvector following method (see Cerjan et al., 1981; Simons et al., 1983; Banerjee et al., 1985; and Baker, 1986; cited above). Thus, by modelling historical/current data with multi-dimensional spline functions, the methodology may be applied to discern the highs, lows and transition paths taken between them. This would allow the prediction of the effects of changes in various parameters in a predictive manner. In other words, sophisticated models allow a trader to set up positions, load and run tests and simulate results.

Steps involved in applying the current invention to the analysis of financial market data include:

1) Obtain the data (historical, current or modelled) and use methods known in the art to transform into n-dimensional arrays for the desired property.
2) Fit n-dimensional spline functions to the respective arrays to give a continuous function.
3) Employ the embodiments described herein on the spline functions.
4) Direct output to the desired method for presentation or for further analysis to discover additional relationships or make predictions.

EXAMPLE 9

MORPHY source code is identified, and provided, at the Elsevier Science Internet web site in the CPC international Program library as "MORPHY, a program for an automated "Atoms in Molecules" analysis, P. L. A. Popelier."

EXAMPLE 10

MORPHY Source Code—see attached Appendix I.

EXAMPLE 11

MORDEN source code—see attached Appendix II.

Those skilled in the art will appreciate that the invention is not limited by what has been particularly shown and described herein as numerous modifications and variations may be made to the preferred embodiment without departing from the spirit and scope of the invention.

We claim:

1. A method of determining the multi-dimensional topology of a system within a space from a set of relative values for scalar properties of the space, each value for a given point within the space, the method comprising the steps of:
    a) interpolating a set of functions to generate continuous relative values for the scalar properties;
    b) identifying critical points of the continuous relative values by using an eigenvector following method;
    c) associating critical points with one another by following a gradient path of the continuous relative values between the critical points; and
    d) generating a representation of the topology according to the associated critical points, wherein the system is the flow of a fluid over a surface.

2. A method of determining the multi-dimensional topology of a system within a space from a set of relative values for scalar properties of the space, each value for a given point within the space, the method comprising the steps of:
    a) interpolating a set of functions to generate continuous relative values for the scalar properties;
    b) identifying critical points of the continuous relative values by using an eigenvector following method;
    c) associating critical points with one another by following a gradient path of the continuous relative values between the critical points; and
    d) generating a representation of the topology according to the associated critical points, wherein the system is the reaction and/or folding of a protein or protein complex.

3. A method of determining the multi-dimensional topology of a system within a space from a set of relative values for scalar properties of the space, each value for a given point within the space, the method comprising the steps of:
    a) interpolating a set of functions to generate continuous relative values for the scalar properties;
    b) identifying critical points of the continuous relative values by using an eigenvector following method;
    c) associating critical points with one another by following a gradient path of the continuous relative values between the critical points; and
    d) generating a representation of the topology according to the associated critical points, wherein the system is an edge portion of a graphical image.

4. A method of determining the multi-dimensional topology of a system within a space from a set of relative values for scalar properties of the space, each value for a given point within the space, the method comprising the steps of:
    a) interpolating a set of functions to generate continuous relative values for the scalar properties;
    b) identifying critical points of the continuous relative values by using an eigenvector following method;
    c) associating critical points with one another by following a gradient path of the continuous relative values between the critical points; and
    d) generating a representation of the topology according to the associated critical points, wherein the system is one or more extremal points within a scalar field.

5. A method of determining the multi-dimensional topology of a system within a space from a set of relative values for scalar properties of the space, each value for a given point within the space, the method comprising the steps of:
    a) interpolating a set of functions to generate continuous relative values for the scalar properties;
    b) identifying critical points of the continuous relative values by using an eigenvector following method;
    c) associating critical points with one another by following a gradient path of the continuous relative values between the critical points; and
    d) generating a representation of the topology according to the associated critical points, wherein the system is a trend or energy surface within a set of data.

6. A method of determining the multi-dimensional topology of a system within a space, having continuous relative values of scalar properties for the space generated from a set of functions interpolating a set of acquired relative values of the scalar properties, each value for a given location within the space, the method comprising the steps of:
    a) identifying critical points of the continuous relative values by using an eigenvector following method;
    b) associating critical points with one another by following a gradient path of the continuous relative values between the critical points; and
    c) generating a representation of the topology according to the associated critical points, wherein the system is the flow of a fluid over a surface.

7. A method of determining the multi-dimensional topology of a system within a space, having continuous relative values of scalar properties for the space generated from a set of functions interpolating a set of acquired relative values of the scalar properties, each value for a given location within the space, the method comprising the steps of:
    a) identifying critical points of the continuous relative values by using an eigenvector following method;
    b) associating critical points with one another by following a gradient path of the continuous relative values between the critical points; and
    c) generating a representation of the topology according to the associated critical points, wherein the system is the reaction and/or folding of a protein or protein complex.

8. A method of determining the multi-dimensional topology of a system within a space, having continuous relative values of scalar properties for the space generated from a set of functions interpolating a set of acquired relative values of the scalar properties, each value for a given location within the space, the method comprising the steps of:
    a) identifying critical points of the continuous relative values by using an eigenvector following method;
    b) associating critical points with one another by following a gradient path of the continuous relative values between the critical points; and
    c) generating a representation of the topology according to the associated critical points, wherein the system is an edge portion of a graphical image.

9. A method of determining the multi-dimensional topology of a system within a space, having continuous relative values of scalar properties for the space generated from a set of functions interpolating a set of acquired relative values of the scalar properties, each value for a given location within the space, the method comprising the steps of:

a) identifying critical points of the continuous relative values by using an eigenvector following method;

b) associating critical points with one another by following a gradient path of the continuous relative values between the critical points; and c) generating a representation of the topology according to the associated critical points, wherein the system is one or more extremal points within a scalar field.

10. A method of determining the multi-dimensional topology of a system within a space, having continuous relative values of scalar properties for the space generated from a set of functions interpolating a set of acquired relative values of the scalar properties, each value for a given location within the space, the method comprising the steps of:

a) identifying critical points of the continuous relative values by using an eigenvector following method;

b) associating critical points with one another by following a gradient path of the continuous relative values between the critical points; and c) generating a representation of the topology according to the associated critical points, wherein the system is a trend or energy surface within a set of data.

* * * * *